US009265798B2

(12) United States Patent  (10) Patent No.: US 9,265,798 B2
Matheny  (45) Date of Patent: *Feb. 23, 2016

(54) METHOD AND SYSTEM FOR TREATMENT OF CARDIOVASCULAR DISORDERS

(71) Applicant: CorMatrix Cardiovascular, Inc., Roswell, GA (US)

(72) Inventor: Robert G Matheny, Norcross, GA (US)

(73) Assignee: CORMATRIX CARDIOVASCULAR, INC, Roswell, GA (US)

( * ) Notice: Subject to any disclaimer, the term of this patent is extended or adjusted under 35 U.S.C. 154(b) by 75 days.

This patent is subject to a terminal disclaimer.

(21) Appl. No.: 14/711,429

(22) Filed: May 13, 2015

(65) Prior Publication Data

US 2015/0238535 A1  Aug. 27, 2015

Related U.S. Application Data

(60) Continuation of application No. 13/915,203, filed on Jun. 11, 2013, which is a division of application No. 13/782,115, filed on Mar. 1, 2013, and a continuation-in-part of application No. 13/573,569, filed on Sep. 24, 2012, and a continuation-in-part of application No. 11/334,631, filed on Jan. 18, 2006.

(51) Int. Cl.
| | |
|---|---|
| *C12N 5/00* | (2006.01) |
| *A61F 2/00* | (2006.01) |
| *A61K 35/37* | (2015.01) |
| *A61K 35/38* | (2015.01) |
| *C12N 5/071* | (2010.01) |
| *C12N 5/02* | (2006.01) |
| *A61K 35/35* | (2015.01) |
| *A61K 45/06* | (2006.01) |
| *A61K 35/12* | (2015.01) |
| *A61L 27/36* | (2006.01) |
| *A61K 48/00* | (2006.01) |
| *A61K 38/18* | (2006.01) |
| *A61L 27/38* | (2006.01) |
| *A61L 27/54* | (2006.01) |
| *A61M 1/12* | (2006.01) |

(52) U.S. Cl.
CPC ............... *A61K 35/35* (2013.01); *A61K 35/12* (2013.01); *A61K 38/18* (2013.01); *A61K 38/185* (2013.01); *A61K 38/1808* (2013.01); *A61K 38/1841* (2013.01); *A61K 38/1866* (2013.01); *A61K 45/06* (2013.01); *A61K 48/00* (2013.01); *A61L 27/3604* (2013.01); *A61L 27/367* (2013.01); *A61L 27/3629* (2013.01); *A61L 27/3633* (2013.01); *A61L 27/3826* (2013.01); *A61L 27/3834* (2013.01); *A61L 27/54* (2013.01); *A61M 1/122* (2014.02); *A61L 2300/414* (2013.01); *A61L 2300/434* (2013.01); *A61L 2300/64* (2013.01); *A61L 2430/20* (2013.01); *A61M 2205/05* (2013.01)

(58) Field of Classification Search
None
See application file for complete search history.

(56) References Cited

U.S. PATENT DOCUMENTS

| | | | |
|---|---|---|---|
| 2005/0031691 A1* | 2/2005 | McGurk et al. | 424/484 |
| 2005/0058688 A1* | 3/2005 | Boerger et al. | 424/426 |
| 2005/0169960 A1* | 8/2005 | Hunter et al. | 424/423 |

(Continued)

*Primary Examiner* — Chris R Tate
*Assistant Examiner* — Douglas F White
(74) *Attorney, Agent, or Firm* — Francis Law Group

(57) ABSTRACT

Methods for treating a cardiovascular disorder comprising administration of one or more extracellular matrix (ECM) based compositions directly to damaged or diseased cardiovascular tissue associated with the cardiovascular disorder, and provision of ventricular assistance.

2 Claims, 4 Drawing Sheets

(56) References Cited

U.S. PATENT DOCUMENTS

| | | | |
|---|---|---|---|
| 2005/0182465 A1* | 8/2005 | Ness | 607/116 |
| 2006/0002979 A1* | 1/2006 | Ashammakhi et al. | 424/426 |
| 2006/0204738 A1* | 9/2006 | Dubrow et al. | 428/292.1 |
| 2007/0014773 A1* | 1/2007 | Matheny et al. | 424/93.21 |

* cited by examiner

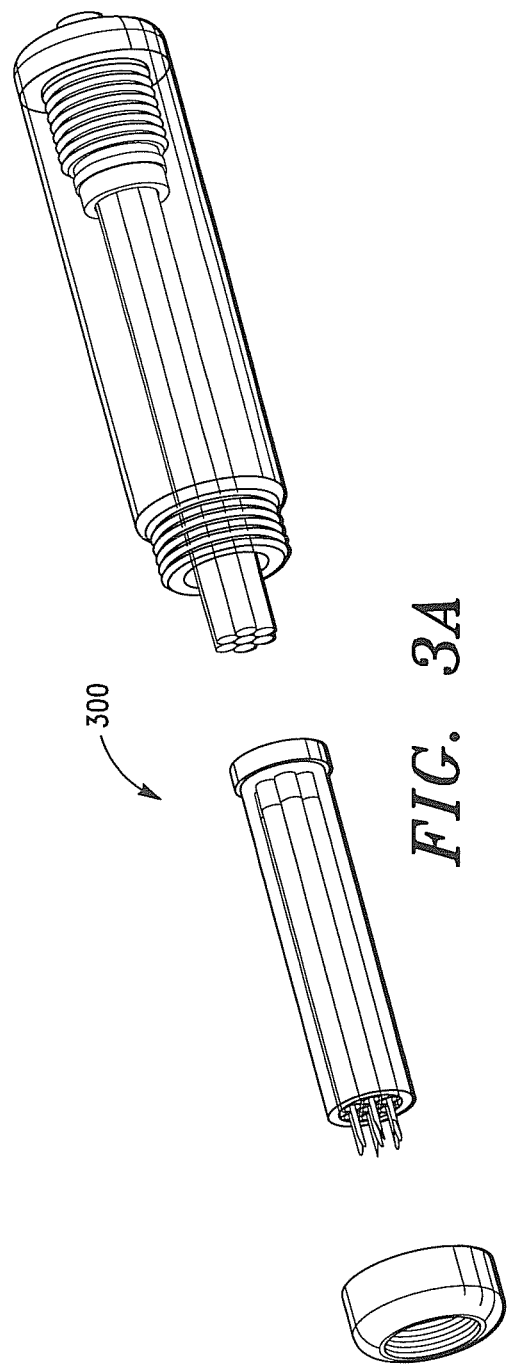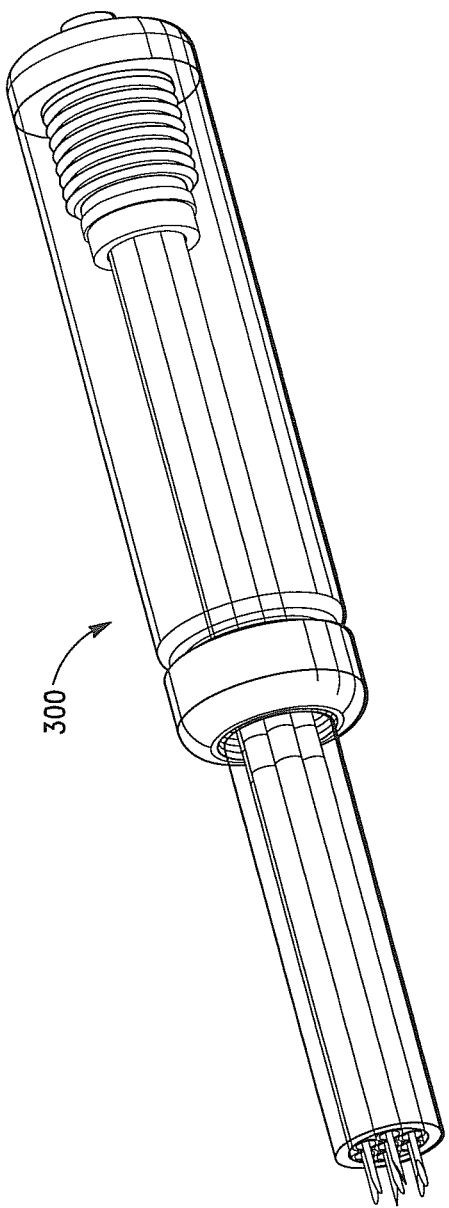
FIG. 3A
FIG. 3B

METHOD AND SYSTEM FOR TREATMENT OF CARDIOVASCULAR DISORDERS

CROSS-REFERENCES TO RELATED APPLICATIONS

This application is a continuation of U.S. application Ser. No. 13/915,203, filed on Jun. 11, 2013, which is a divisional of U.S. application Ser. No. 13/782,115, filed on Mar. 1, 2013, which is a continuation-in-part of U.S. application Ser. No. 13/573,569, filed on Sep. 24, 2012, which is a continuation-in-part of U.S. application Ser. No. 11/334,631, filed on Jan. 18, 2006.

FIELD OF THE INVENTION

The present invention relates to methods for treating cardiovascular disorders. More particularly, the present invention relates to methods for treating cardiovascular disorders comprising concomitant administration of an extracellular matrix (ECM) composition and ventricular assistance.

BACKGROUND OF THE INVENTION

As is well known in the art, heart failure can be caused by a diverse array of cardiovascular disorders that reduce the efficiency of the myocardium, including ischemic heart disease, coronary artery disease, and a defective or diseased heart valve. Among the noted disorders, ischemic heart disease, which commonly presents as a myocardial infarction, is the leading cause of heart failure.

Indeed, in 2004 alone, the World Health Organization estimated that 12.2% of worldwide deaths occurred as a result of ischemic heart disease. Ischemic heart disease was also deemed the leading cause of death in middle to high income countries and second only to respiratory infections in lower income countries. *The Global Burden of Disease: World Health Organization* 2004 *Update*, Geneva (2008). Worldwide more than 3 million people present with a ST elevation myocardial infarction (STEMI) and 4 million people present with a non-ST elevation myocardial infarction (NSTEMI) a year. White, et al., *Acute Myocardial Infarction*, Lancet 372 (9638), pp. 570-84 (August 2008).

Rates of death from ischemic heart disease have slowed or declined in most high income countries, although cardiovascular disease still accounted for 1 in 3 of all deaths in the USA in 2008. Roger, et al., *Executive summary: Heart Disease and Stroke Statistics*—2012 *update: A report from the American Heart Association*, Circulation 125 (1), pp. 188-97 (January 2012).

In contrast, ischemic heart disease is becoming a more common cause of death in the developing world. For example in India, ischemic heart disease had become the leading cause of death by 2004; accounting for 1.46 million deaths (14% of total deaths). Deaths in India due to ischemic heart disease were also expected to double during 1985-2015. Gupta, et al., *Epidemiology and Causation of Coronary Heart Disease and Stroke in India*, Heart 94 (1), pp. 16-26 (January 2008).

Globally, it is predicted that disability adjusted life years (DALYs) lost to ischemic heart disease will account for 5.5% of total DALYs in 2030, making it the second most important cause of disability (after unipolar depressive disorder), as well as the leading cause of death by this date.

Ischemic heart disease often occurs when myocardial tissue is no longer receiving adequate blood flow. Various methods for treating ischemic heart disease have thus been developed. Such methods include systemic delivery of various pharmacological agents.

Several additional methods for treating ischemic heart disease are directed to re-establishing blood flow to the ischemic area. Such methods include stimulation of angiogenesis and surgical intervention, e.g. bypass surgery or angioplasty. Other methods include the use of lasers to bore holes through the ischemic area(s) to promote blood flow. As one can readily appreciate, there are numerous incumbent risks associated with the noted methods.

A further method for treating ischemic heart disease is the direct delivery of bioactive or pharmacological agents to the ischemic area. Illustrative is the delivery of extracellular matrix (ECM) based compositions directly to cardiovascular tissue disclosed in Co-pending application Ser. No. 13/573,569.

More recently, ventricular assist devices (VADs) have been employed as treatment platforms for various pharmacological therapies, e.g. stem cell administration, which have been developed to treat cardiovascular disorders, including ischemic heart disease. VADs are designed to support (or augment) the function of either the right (RVAD) or left (LVAD) ventricle, or both at once (BiVAD). The type of VAD employed depends primarily on the underlying cardiovascular disorder, and the pulmonary arterial resistance that determines the load on the right ventricle.

Although the direct delivery of bioactive or pharmacological agents; particularly, the ECM based compositions disclosed in Co-pending application Ser. No. 13/573,569, and other treatment therapies employing ventricular assistance have been found effective to treat cardiovascular disorders and, thereby, heart failure, there remains a need to provide even more effective means for treating cardiovascular disorders.

It is therefore an object of the present invention to provide improved methods for treating cardiovascular disorders.

It is another object of the present invention to provide methods for treating cardiovascular disorders that include concomitant administration of an ECM based composition and ventricular assistance.

It is another object of the present invention to provide methods for treating cardiovascular disorders that include concomitant administration of (i) an ECM based composition, which, when delivered to damaged biological tissue; particularly, cardiovascular tissue, induces neovascularization, host tissue proliferation, bioremodeling, and regeneration of cardiovascular tissue and associated structures with site-specific structural and functional properties, and (ii) ventricular assistance to augment heart function.

SUMMARY OF THE INVENTION

The present invention is directed to methods and systems for treating cardiovascular disorders. In a preferred embodiment of the invention, the methods comprise concomitant administration of one or more ECM based compositions to damaged or diseased cardiovascular tissue, and provision of ventricular assistance.

In a preferred embodiment of the invention, one or more ECM based compositions are administered directly to the cardiovascular tissue.

In some embodiments, the cardiovascular tissue comprises myocardium tissue.

In a preferred embodiment, the ECM based compositions include at least one ECM material derived from a mammalian tissue source.

In some embodiments, the mammalian tissue source is selected from the group comprising small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornomentum extracellular matrix, cardiac extracellular matrix, e.g., pericardium and/or myocardium, kidney extracellular matrix, pancreas extracellular matrix, lung extracellular matrix, and combinations thereof.

In a preferred embodiment, the mammalian tissue source comprises mesothelial tissue.

In some embodiments, the ECM compositions further include one or more additional biologically active components to facilitate treatment of the damaged cardiovascular tissue and/or the tissue regenerative process.

In some embodiments, the biologically active component comprises a pharmacological agent or composition.

In some embodiments of the invention, the biologically active component comprises an anti-inflammatory agent or composition.

In some embodiments of the invention, the biologically active component comprises a statin selected from the group comprising atorvastatin, cerivastatin, fluvastatin, lovastatin, mevastatin, pitavastatin, pravastatin, rosuvastatin, and simvastatin.

In some embodiments of the invention, the biologically active component comprises a growth factor selected from the group comprising a platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platlet derived growth factor (PDGF), tumor necrosis factor alpha (TNA-alpha), and placental growth factor (PLGF).

In some embodiments of the invention, the biologically active component comprises an anti-arrhythmic agent selected from the group comprising quinidine, procainamide, disopyramide, lidocaine, phenytoin, mexiletine, flecainide, propafenone, moricizine, propranolol, esmolol, timolol, metoprolol, atenolol, amiodarone, sotalol, ibutilide, dofetilide, verapamil, diltiazem, adenosine and digoxin.

In some embodiments of the invention, the biologically active component comprises a protein.

In some embodiments of the invention, the ECM based compositions are formulated to facilitate injection of the ECM based compositions to damaged or diseased tissue (i.e. injectable ECM compositions).

In some embodiments of the invention, ventricular assistance is provided by a mechanical circulatory support (MCS) device.

In some embodiments of the invention, ventricular assistance is provided by a left ventricular assist device (LVAD).

In some embodiments of the invention, ventricular assistance is provided by a right ventricular assist device (RVAD).

In some embodiments of the invention, ventricular assistance is provided by a left and right ventricular assist device (BiVAD).

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 3A is an exploded perspective view of one embodiment of a multi-needle injection apparatus that is suitable for direct administration of ECM compositions to biological tissue, e.g. cardiovascular tissue, in accordance with the invention;

FIG. 3B is an assembled perspective view of the multi-needle injection apparatus shown in FIG. 3A, in accordance with the invention;

DETAILED DESCRIPTION OF THE PREFERRED EMBODIMENT

Figure 1:
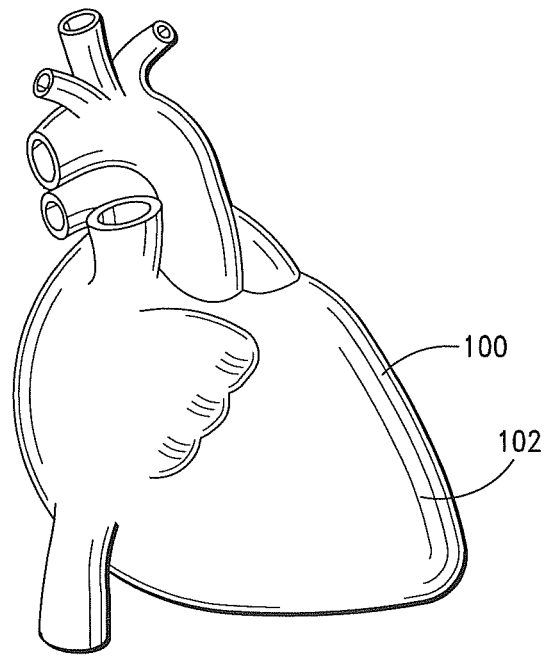
FIG. 1 is a depiction of a normal heart.

Before describing the present invention in detail, it is to be understood that this invention is not limited to particularly exemplified apparatus, systems, compositions or methods as such may, of course, vary. Thus, although a number of systems, compositions and methods similar or equivalent to those described herein can be used in the practice of the present invention, the preferred systems, compositions and methods are described herein.

It is also to be understood that, although a preferred method of delivering an ECM based composition of the invention to biological tissue comprises direct injection into the tissue. The delivery of an ECM based composition is not limited to direct injection. According to the invention, an ECM based composition of the invention can be delivered to biological tissue by other conventional means, including topical administration.

It is further to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a, "an" and "the" include plural referents unless the content clearly dictates otherwise. Thus, for example, reference to "an anti-inflammatory" includes two or more such agents and the like.

DEFINITIONS

The terms "cardiovascular disorder" and "heart failure" are used interchangeably herein, and mean and include any abnormal function of the heart; particularly, abnormal functions or deficiency of the myocardium. The terms "cardiovascular disorder" and "heart failure" thus include, without limitation, ischemic heart disease, coronary artery disease, a defective or diseased heart valve, myocarditis, an inflammatory disease, cardiomyopathy and amyloidosis.

The term "ventricular assistance", as used herein, means and includes any means of providing circulatory assistance to a heart and/or supporting the function of a heart. According to the invention, "ventricular assistance" can be provided by a variety of conventional ventricular assist devices, including, without limitation, a left ventricular assist device (LVAD), right ventricular assist device (RVAD), left and right ventricular assist device (BiVAD), and other mechanical circulatory support (MCS) devices.

The term "concomitant", as used herein in connection with the administration of an ECM based composition of the invention and ventricular assistance, means that the ECM based composition and ventricular assistance are administered (or provided) concurrently at a defined point in time. Thus, in some embodiments of the invention, ventricular assistance is initially provided followed by the administration of an ECM based composition. In some embodiments, an ECM based composition is initially administered and ventricular assistance is provided thereafter.

The terms "cardiovascular tissue damage," "cardiac tissue damage," and "cardiac tissue injury" and are used interchangeably herein, and mean and include any area of abnormal tissue in the cardiovascular system or heart caused by a disease, disorder, injury or damage, including damage to the epicardium, endocardium and/or myocardium.

As is well known in the art, cardiovascular tissue damage most often involves damage or injury to the myocardium and, therefore, for the purposes of this disclosure, myocardial damage or injury is equivalent to cardiovascular tissue damage.

The terms "prevent" and "preventing" are used interchangeably herein, and mean and include reducing the frequency or severity of a disease, condition or disorder. The term does not require an absolute preclusion of the disease, condition or disorder. Rather, this term includes decreasing the chance for disease occurrence.

The terms "treat" and "treatment" are used interchangeably herein, and mean and include medical management of a patient with the intent to cure, ameliorate, stabilize, or prevent a disease, pathological condition or disorder. The terms include "active treatment", i.e. treatment directed specifically toward the improvement of a disease, pathological condition or disorder, and "causal treatment", i.e. treatment directed toward removal of the cause of the associated disease, pathological condition or disorder.

The terms "treat" and "treatment" further include "palliative treatment", i.e. treatment designed for the relief of symptoms rather than the curing of the disease, pathological condition or disorder, "preventative treatment", i.e. treatment directed to minimizing or partially or completely inhibiting the development of the associated disease, pathological condition or disorder, and "supportive treatment", i.e. treatment employed to supplement another specific therapy directed toward the improvement of the associated disease, pathological condition or disorder.

The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, the ECM material can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornomentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM material can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

According to the invention, ECM material can comprise, in whole or in part, just the basement membrane (or transitional epithelial layer) with the subadjacent tunica propria, the tunica submucosa, tunica muscularis, and tunica serosa. The extracellular matrix component of the ECM material can thus contain any or all of these layers or only the basement membrane portion, excluding the submucosa.

The term "chamber remodeling", as used herein, means and includes a series of events (which may include changes in gene expression, molecular, cellular and interstitial changes) that result in changes in size, shape and function of biological tissue following stress or injury. As is well known in the art, remodeling can occur after a myocardial infarction, pressure overload (e.g., aortic stenosis, hypertension), volume overload (e.g., valvular regurgitation), inflammatory heart disease (e.g., myocarditis), or in idiopathic cases (e.g., idiopathic dilated cardiomyopathy).

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The terms "pharmacological agent", "pharmacological composition" and "biologically active agent", as used herein, mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent" and "biologically active agent" thus mean and include, without limitation, antibiotics, anti-arrhythmic agents, anti-viral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent" and "biologically active agent" accordingly include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, Anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

According to the invention, the terms "pharmacological agent" and "biologically active agent" further include, without limitation, the following growth factors: platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platlet derived growth factor (PDGF), tumor necrosis factor alpha (TNA-alpha), and placental growth factor (PLGF).

The terms "pharmacological agent" and "biologically active agent" further include, without limitation, the following Class I—Class V antiarrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent" and "biologically active agent" further include, without limitation, the following antibiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent" and "biologically active agent" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent" and "biologically active agent" further include, without limitation, the following narcotic analgesics: morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent" and "biologically active agent" further include, without limitation, the following anesthetics: esters, such as benzocaine, chloroprocaine, cocaine, cyclomethycaine, dimethocaine/larocaine, piperocaine, propoxycaine, procaine/novacaine, proparacaine, and tetracaine/amethocaine. Local anesthetics can also include, without limitation, amides, such as articaine, bupivacaine, cinchocaine/dibucaine, etidocaine, levobupivacaine, lidocaine/lignocaine, mepivacaine, prilocaine, ropivacaine, and trimecaine. Local anesthetics can further include combinations of the above from either amides or esters.

The terms "pharmacological agent" and "biologically active agent" further include, without limitation, the following cytotoxic anti-neoplastic agents and chemotherapy agents: alkylating agents, cisplatin, carboplatin, oxaliplatin, mechlorethamine, cyclophosphamide, chlorambucil, and Ifosfamide. Chemotherapy agents can also include, without limitation, antimetabolites, such as purine analogues, pyrimidine analogues, and antifolates, plant alkaloids, such as vincristine, vinblastine, vinorelbine, vindesine, podophyllotoxin, etoposide and teniposide, taxanes, such as paclitaxel and docetaxel, topoisomerase inhibitors, such as irinotecan, topotecan, amsacrine, etoposide, etoposide phosphate and teniposide, cytotoxic antibiotics, such as actinomyocin, bleomycin, plicamycin, mytomycin and anthracyclines, such as doxorubicin, daunorubicin, valrubicin, idarubicin, epirubicin, and antibody treatments, such as abciximab, adamlimumab, alamtuzumab, basiliximab, belimumab, bevacizumab, brentuximab vedotin, canakinumab, cetuximab, certolizumab pego, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumumab, ranibizumab, rituximab, tocilizumab (atlizumab), tositumomab and trastuzumab.

The terms "pharmacological agent" and "biologically active agent" further include, without limitation, the following anti-inflammatories: alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclopro- fen, cintazone, cliprofen, clobetasol propionate, clobetasone butyrate, clopirac, cloticasone propionate, cormethasone acetate, cortodox one, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabtunetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The term "biologically active agent" further includes, without limitation, organisms that have the potential to induce modulating proliferation, and/or growth and/or regeneration of tissue. The terms "biologically active agent" thus includes, without limitation, the following cells: human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and post-natal stem cells.

According to the invention, the terms "pharmacological agent" and "biologically active agent" can further include the following active agents (referred to interchangeably herein as a "protein", "peptide" and "polypeptide"): collagen (types I-V), proteoglycans, glycosaminoglycans (GAGs), glycoproteins, growth factors, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dennatan sulfate), chondroitin sulfate A, heparin sulfates, hyaluronic acids, fibronectins, tenascins, elastins, fibrillins, laminins, nidogen/enactins, fibulin I, finulin II, integrins, transmembrane molecules, thrombospondins, osteopontins, and angiotensin converting enzymes (ACE).

The terms "active agent formulation", "pharmacological agent formulation" and "agent formulation", are also used interchangeably herein, and mean and include a "pharmacological agent" (or "biologically active agent") optionally in combination with one or more pharmaceutically acceptable carriers and/or additional inert ingredients. According to the invention, the formulations can be either in solution or in suspension in the carrier.

The term "pharmacological composition", as used herein, means and includes a composition comprising a "pharmacological agent" and/or "biologically active agent" and/or "pharmacological agent formulation" and/or any additional agent or component identified herein.

The term "therapeutically effective", as used herein, means that the amount of the "pharmacological composition" and/or "biologically active agent" and/or "active agent formulation" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "delivery" and "administration" are used interchangeably herein, and mean and include providing a "pharmacological composition" or "biologically active agent" or "active agent formulation" to a treatment site, e.g., damaged tissue, through any method appropriate to deliver the functional agent or formulation or composition to the treatment site. Non-limiting examples of delivery methods include direct injection, percutaneous delivery and topical application at the treatment site.

The term "percutaneous", as used herein, means and includes any penetration through the skin of a patient or subject, whether in the form of a small cut, incision, hole, cannula, tubular access sleeve or port or the like.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As indicated above, the present disclosure is directed to methods and systems for treating cardiovascular disorders. In a preferred embodiment of the invention, the methods comprise concomitant administration of one or more ECM based compositions to damaged or diseased cardiovascular tissue, and provision of ventricular assistance.

As also indicated above and discussed in detail herein, the term "concomitant" means that an ECM based composition and ventricular assistance are administered (or provided) concurrently at a defined point in time.

Thus, in some embodiments of the invention, ventricular assistance is initially provided followed by the administration of an ECM based composition.

According to the invention, the pre-ECM delivery time period can promptly after administering ventricular assistance to, minutes, hours or days after administering ventricular assistance.

In some embodiments, an ECM based composition is initially administered and ventricular assistance is provided thereafter.

In a preferred embodiment of the invention, the ECM based compositions include at least one extracellular matrix (hereinafter "ECM material").

According to the invention, the ECM material can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety. The mammalian tissue sources include, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, omamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The ECM material can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

According to the invention, the ECM compositions of the invention can also comprise ECM material from two or more mammalian sources. Thus, for example, the composition can comprise ECM material combinations from such sources as, for example, but not limited to, small intestine submucosa, liver basement membrane, stomach submucosa, urinary bladder submucosa, placental basement membrane, pancreatic basement membrane, large intestine submucosa, lung interstitial membrane, respiratory tract submucosa, heart ECM material, dermal matrix, and, in general, ECM material from any mammalian fetal tissue. The ECM material sources can also comprise different mammalian animals or an entirely different species of mammals.

The ECM material can also be used in whole or in part, so that, for example, an ECM material can contain just the basement membrane (or transitional epithelial layer) with the subadjacent tunica propria, the tunica submucosa, tunica muscularis, and tunica serosa. The ECM material component of the composition can contain any or all of these layers, and thus could conceivably contain only the basement membrane portion, excluding the submucosa. However, generally, and especially since the submucosa is thought to contain and support the active growth factors and other proteins necessary for in vivo tissue regeneration, the ECM or matrix composition from any given source will contain the active extracellular matrix portions that support cell development and differentiation and tissue regeneration.

According to the invention, the ECM based compositions can comprise mixed liquids, mixed emulsions, mixed gels, mixed pastes, or mixed solid particulates. Suitable ECM based compositions are set forth in Co-pending application Ser. Nos. 11/182,551, 11/448,351, 11/334,631, 13/033,053, 13/573,569 and 13/732,943; which are incorporated herein in their entirety.

According to the invention, the ECM based compositions of the invention can further include one or more pharmacological agents or compositions, and/or one or more bioactive agents or components that aid in the treatment of damaged tissue and/or facilitate the tissue regenerative process.

In some embodiments, the ECM based compositions thus include at least one pharmacological agent or composition, which can comprise, without limitation, antibiotics or anti-fungal agents, anti-viral agents, anti-pain agents, anesthetics, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

Suitable pharmacological agents and/or compositions accordingly include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, Anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

According to the invention, the amount of a pharmacological agent added to an ECM composition of the invention will, of course, vary from agent to agent. For example, in one embodiment, wherein the pharmacological agent comprises diclofenac (Voltaren®), the amount of diclofenac included in the ECM composition is preferably in the range of 10 µg-75 mg.

In some embodiments of the invention, the pharmacological agent specifically comprises an anti-inflammatory agent. According to the invention, suitable anti-inflammatory agents include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sennetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

According to the invention, the amount of an anti-inflammatory added to an ECM composition of the invention can similarly vary from anti-inflammatory to anti-inflammatory. For example, in one embodiment of the invention, wherein the pharmacological agent comprises ibuprofen (Advil®), the amount of ibuprofen included in the ECM composition is preferably in the range of 100 μg-200 mg.

In some embodiments of the invention, the ECM based compositions include a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

Applicant has found that the noted statins exhibit numerous beneficial properties that provide several beneficial biochemical actions or activities. Several significant properties and beneficial actions resulting therefrom are discussed in detail below. Additional properties and beneficial actions are set forth in Co-Pending application Ser. No. 13/373,569, filed on Sep. 24, 2012; which is incorporated by reference herein in its entirety.

Anti-Inflammatory Properties/Actions

Statins have numerous favorable effects on vascular wall cells and the cardiovascular system. One specific example is that statins facilitate the reduction of the G-Protein-Coupled Receptor, thromboxane A2 (TXA2), which lowers the platelet activation and aggregation, and augmentation of adhesion molecules and chemokines.

Statins further impact vascular wall cells and the cardiovascular system by blocking ras homilog gene family, member A (RhoA) activation. Blocking RhoA activation further impacts numerous systems, such as macrophage growth, tissue plasminogen activators (t-PA), plasminogen activator inhibitor type 1 (PAI-1), smooth muscle cell (SMC) proliferation, nitric oxide (NO) production, endothelins, and angiotensin receptors.

Macrophage growth reduced by blocking RhoA activation results in the reduction of matrix metalloprotinases (MMPs) and tissue factors (TF). Lowered MMPs also results in a lowered presence of thrombi, as the MMPs attach to ECM present in thrombi or damaged ECM at wound sites.

Fibrinolysis Properties/Actions

Blocking RhoA activation also affects the presence of tissue plasminogen activators (t-PA) and plasminogen activator inhibitor type 1 (PAI-1), which is the principal inhibitor of fibrinolysis. With t-PA presence raised and PAI-1 diminished from the blocking of RhoA activation induced by statins, a reduced thrombotic effect is realized due to reduced opportunity for fibrin to form the polymeric mesh of a hemostatic plug.

NO Regulation Properties/Actions

Blocking RhoA activation also affects the presence of Nitric Oxide (NO) in the cardiovascular system. NO contributes to vessel homeostasis by inhibiting vascular smooth muscle contraction and growth, platelet aggregation, and leukocyte adhesion to the endothelium.

RhoA Activation Blocking Properties/Actions

The administration of statins can also enhance the presence of endothelins and angiotensin receptors. Endothelins and angiotensin receptors can also be affected by the subsequent blocking of RhoA activation associated with statin administration.

There are three isoforms of endothelins; ET-1, ET-2, and ET-3, with ET-1 being the isoform primarily affected by statins and RhoA activation blocking. Secretion of ET-1 from the endothelium signals vasoconstriction and influences local cellular growth and survival.

Angiotensin receptors are protein coupled receptors that are responsible for the signal transduction of the vasoconstricting stimulus of the main effector hormone angiotensin II. Angiotensin Receptor II Type I (AT-1) is the angiotensin receptor primarily affected by statin administration and RhoA activation blocking. AT-1 mediates vasocontraction, cardiac hypertrophy, vascular smooth muscle cell proliferation, inter alia.

C-Reactive Protein Reduction Properties/Actions

C-Reactive Proteins (CRP) are also reduced by statins. CRPs are found in the blood; the levels of which deviate in response to differing levels of inflammation.

Adhesion Molecule Reduction Properties/Actions

Statins also reduce the presence of adhesion molecules on the endothelium. Adhesion molecules are proteins that are located on the cell surface and are involved with inflammation and thrombin formation in vascular endothelial cells.

Rac-1 Reduction Properties/Actions

The expression of Rac-1 is also reduced by statins. Rac-1 is a protein found in human cells, which plays a central role in endothelial cell migration, tubulogenesis, adhesion, and permeability. The decrease in the presence of Rac-1 also results in the decrease of reactive oxygen species (ROS).

According to the invention, the amount of a statin added to an ECM composition of the invention is preferably less than 20 mg, more preferably, less than approximately 10 mg.

In some embodiments of the invention, the ECM based compositions include 100 ug-5 mg of a statin. In some embodiments of the invention, the ECM based compositions include 500 ug-2 mg of a statin.

In some embodiments of the invention, the ECM based compositions include chitosan. As also set forth in detail in Co-Pending application Ser. No. 13/573,569, chitosan also exhibits numerous beneficial properties that provide several beneficial biochemical actions or activities.

According to the invention, the amount of chitosan added to an ECM based composition of the invention is preferably less than 50 ml, more preferably, less than approximately 20 ml.

In some embodiments of the invention, the ECM based compositions include a growth factor. According to the invention, suitable growth factors include, without limitation, a platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platlet derived growth factor (PDGF), tumor necrosis factor alpha (TNA-alpha), and placental growth factor (PLGF).

In some embodiments of the invention, the ECM based compositions include an antiarrhythmic agent. According to the invention, suitable antiarrhythmic agents include, without limitation, quinidine, procainamide, disopyramide, lidocaine, phenytoin, mexiletine, flecainide, propafenone, moricizine, propranolol, esmolol, timolol, metoprolol, atenolol, amiodarone, sotalol, ibutilide, dofetilide, verapamil, diltiazem, adenosine and digoxin.

In some embodiments of the invention, the ECM based compositions include a cell. According to the invention, suitable cells include, without limitation, a human embryonic stem cell, fetal cell, fetal cardiomyocyte, myofibroblast, mesenchymal stem cell, autotransplanted expanded cardiomyocyte, adipocyte, totipotent cell, pluripotent cell, blood stem cell, myoblast, adult stem cell, bone marrow cell, mesenchymal cell, embryonic stem cell, parenchymal cell, epithelial cell, endothelial cell, mesothelial cell, fibroblast, myofibroblast, osteoblast, chondrocyte, exogenous cell, endogenous cell, stem cell, hematopoetic stem cell, pluripotent stem cell, bone marrow-derived progenitor cell, progenitor cell, myocardial cell, skeletal cell, undifferentiated cell, multi-potent progenitor cell, unipotent progenitor cell, monocyte, cardiomyocyte, cardiac myoblast, skeletal myoblast, macrophage, capillary endothelial cell, xenogenic cell and allogenic cell.

In some embodiments of the invention, the ECM based compositions include a protein. According to the invention, the protein can comprise, without limitation, a growth factor, collagen, proteoglycan, glycosaminoglycan (GAG) chain, glycoprotein, cytokine, cell-surface associated protein, cell adhesion molecule (CAM), angiogenic growth factor, endothelial ligand, matrikine, matrix metalloprotease, cadherin, immunoglobin, fibril collagen, non-fibrillar collagen, basement membrane collagen, multiplexin, small-leucine rich proteoglycan, decorin, biglycan, fibromodulin, keratocan, lumican, epiphycan, heparan sulfate proteoglycan, perlecan, agrin, testican, syndecan, glypican, serglycin, selectin, lectican, aggrecan, versican, nuerocan, brevican, cytoplasmic domain-44 (CD44), macrophage stimulating factor, amyloid precursor protein, heparin, chondroitin sulfate B (dennatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-beta), fibroblast growth factor-2 (FGF-2) (also called basic fibroblast growth factor (bFGF)), thrombospondin, osteopontin, angiotensin converting enzyme (ACE), and vascular epithelial growth factor (VEGF).

According to the invention, the pharmacological and bioactive agents referenced above can comprise any form. In some embodiments of the invention, the agents, e.g. simvastatin and/or chitosan, comprise microcapsules that provide delayed delivery of the agent contained therein.

Referring now to FIG. 1, there is shown a depiction of a normal human heart 100. The heart wall 102 consists of an inner layer of simple squamous epithelium, referred to as the endocardium. The endocardium overlays the myocardium (a variably thick heart muscle) and is enveloped within a multilayer tissue structure referred to as the pericardium. The innermost layer of the pericardium, referred to as the visceral pericardium or epicardium, covers the myocardium. An outermost layer of the pericardium, referred to as the fibrous pericardium, attaches the parietal pericardium to the sternum, the great vessels and the diaphragm.

Figure 2:
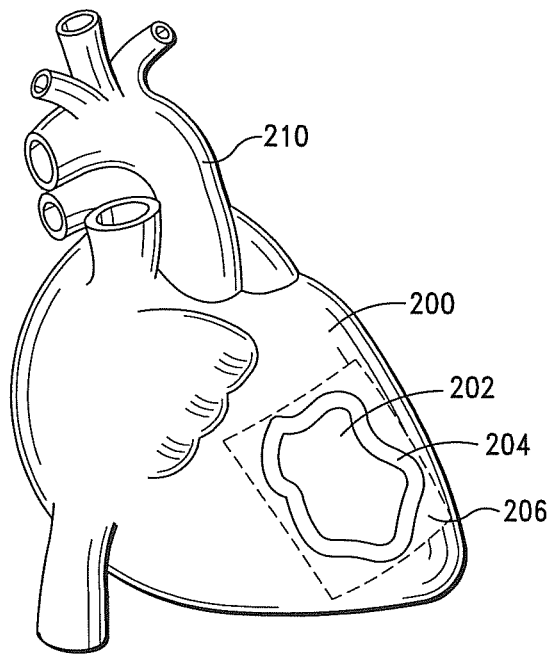
FIG. 2 is a of a heart having an ischemic infracted region.

Referring now to FIG. 2, there is shown a depiction of a heart 200 having an ischemic infarcted region 202, and a peri-infarcted region 204 that is surrounded by healthy non-ischemic myocardium tissue 206.

As indicated above, the ischemic infarcted region 202 (or myocardial infarction) can, and in many instances will trigger a cascading sequence of myocellular events. In many instances, the myocellular events lead to deterioration in ventricular function and heart failure.

As discussed in detail in Co-pending application Ser. No. 13/573,569, the effects of an ischemic infarcted region can be ameliorated or eliminated by delivering an ECM based composition of the invention directly to the infarcted cardiovascular tissue. In most instances, the based ECM compositions will induce neovascularization, host tissue proliferation, bioremodeling, and regeneration of new cardiac tissue structures with site-specific structural and functional properties.

According to the invention, the ECM based compositions can be delivered to infarcted cardiovascular tissue, as well as other damaged or diseased biological tissue, by various conventional means. In some embodiments, a multi-needle injection system, such as disclosed in U.S. Application No. 61/704,634, filed Sep. 24, 2012 and illustrated in FIGS. 3A and 3B is employed to deliver one or more ECM based compositions to damaged or diseased cardiovascular tissue.

Applicants herein have further found that the noted cardiovascular disorder, i.e. ischemic heart disease, as well as other cardiovascular disorders can be effectively treated by the administration of an ECM based composition (and/or a device formed therefrom, e.g. an ECM based patch or endograft) in conjunction with ventricular assistance.

According to the invention, ventricular assistance can be provided by a variety of conventional ventricular assist devices, including, without limitation, a left ventricular assist device (LVAD), right ventricular assist device (RVAD), left and right ventricular assist device (BiVAD), and other mechanical circulatory support (MCS) devices.

Figure 4:
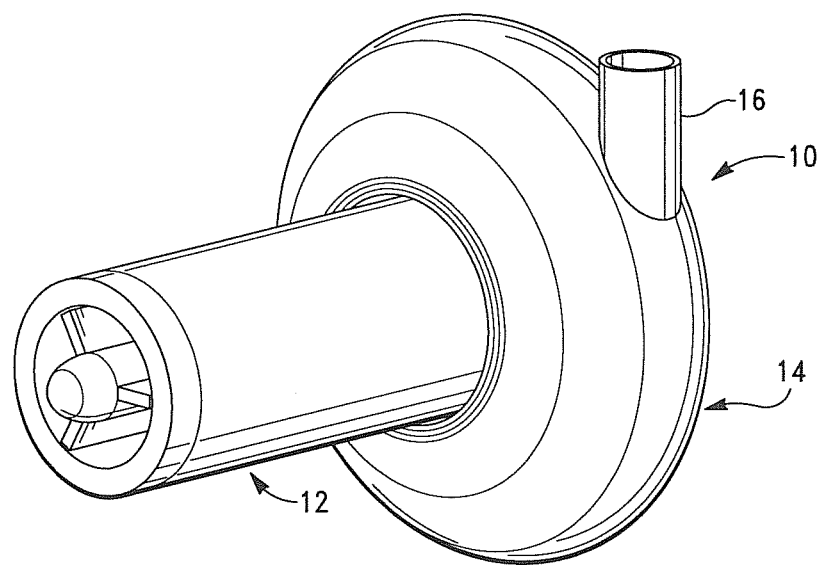
FIG. 4 is a front perspective view of a prior art ventricular assist device (VAD)

In some embodiments of the invention, ventricular assistance is provided by a left ventricular assist device (LVAD), such as the HeartWare HVAD™ device illustrated in FIG. 4. As illustrated in FIG. 4, the HVAD device includes a pump 10 having an elongated inlet 12 and an impeller casing or volute 14. A discharge tube 16 also extends through the pump housing to communicate with the interior of the impeller casing 14.

Figure 5:
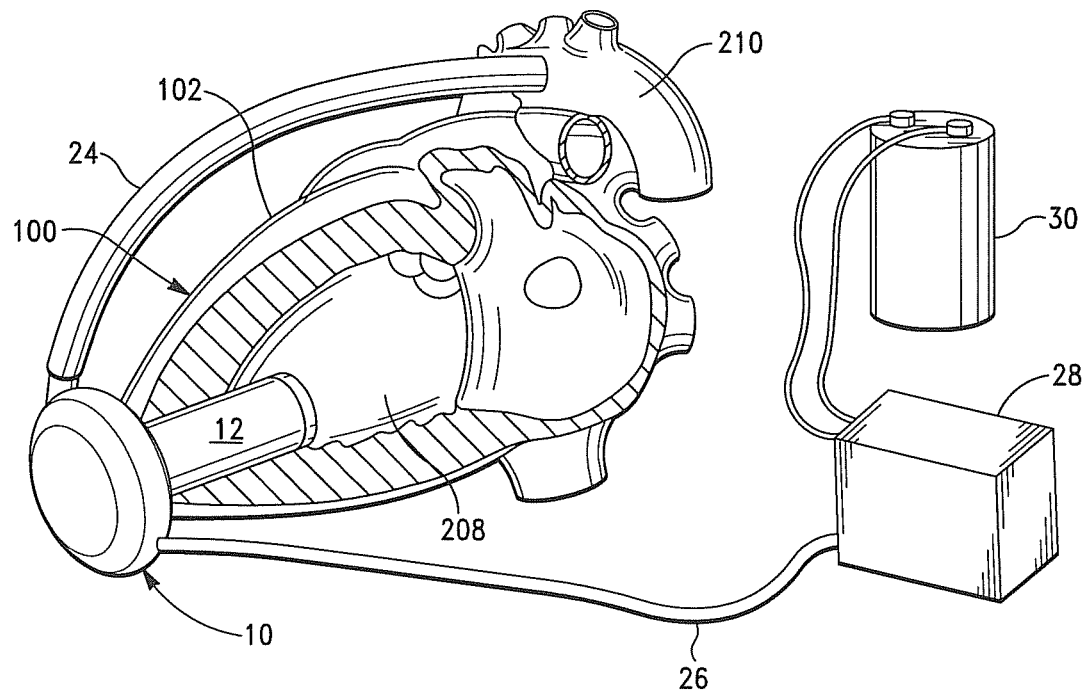
FIG. 5 is a simplified, fragmentary representation of a human heart, showing the VAD illustrated in FIG. 4 implanted within the left ventricle of the heart, in accordance with the invention.

Referring now to FIG. 5, in some applications, the inlet tube 12, which serves as an inflow cannula, is preferably placed into the apex of the left ventricle 208. An arterial graft 212 is connected on one end to discharge tube 16 and on the other end to the aorta 210 through an end-to-end anastomosis.

As illustrated in FIG. 5, the pump 10 further includes a driveline (cable) 26 that connects the implanted pump 10 to an externally worn controller 28. The controller 28, which includes a battery pack 30, regulates the pump 10 and provides the patient with visual and audible indications regarding the operation of the system.

There is thus provided herein methods for treating a cardiovascular disorder comprising concomitant administration of (i) an ECM based composition directly to damaged or diseased cardiovascular tissue associated with the cardiovascular disorder, and (ii) ventricular assistance.

There is also provided herein a system for treating a cardiovascular disorder comprising (i) means for delivering an ECM based composition directly to damaged or diseased cardiovascular tissue associated with the cardiovascular disorder, and (ii) means for providing ventricular assistance or support for the underlying cardiovascular system.

EXAMPLES

The following examples are provided to enable those skilled in the art to more clearly understand and practice the present invention. They should not be considered as limiting the scope of the invention, but merely as being illustrated as representative thereof.

Example 1

Three groups of porcine samples were subjected to three cardiovascular treatments, i.e. ventricular assist (VAD) only, administration of an extracellular matrix (ECM) composition of the invention, and VAD plus administration of the ECM composition after inducing an infarct.

Figure 6:
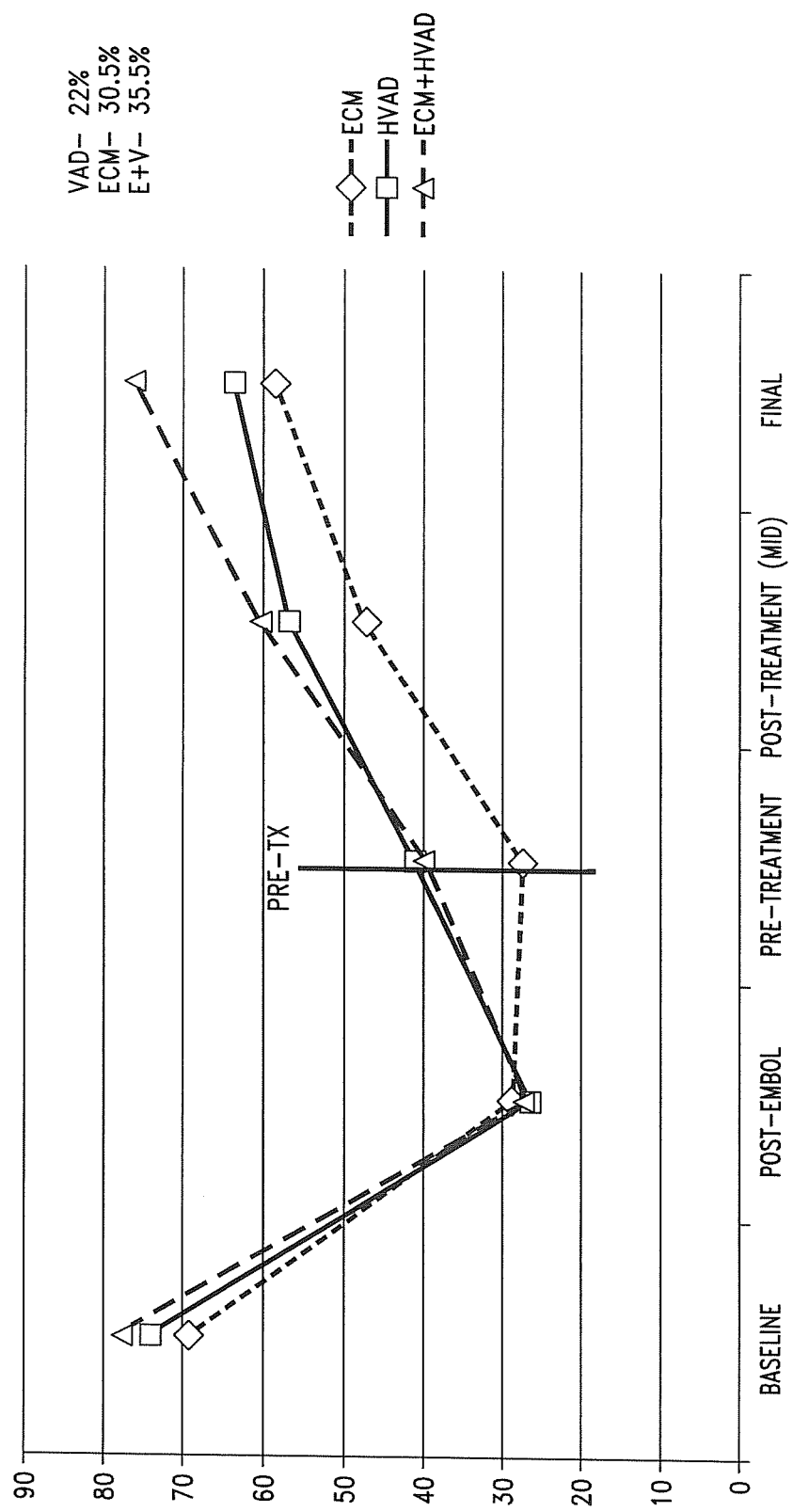
FIG. 6 is a graphical illustration of ejection fraction as a function of time for porcine samples subjected to three cardiovascular treatments, i.e. ventricular assist (VAD) only, administration of an extracellular matrix (ECM) composition, and VAD plus administration of an ECM composition, in accordance with the invention.

Referring now to FIG. 6, there is shown a graphical illustration of ejection fraction as a function of time for the porcine samples. As is well known in the art, ejection fraction indicates what percentage of blood is ejected from the heart with each beat and, hence, is a seminal cardiovascular performance factor. A normal ejection fraction is ≥50%.

As illustrated in FIG. 6, there was a progressive improvement in cardiovascular performance after 60 days between the porcine groups; with the combined therapy of VAD and ECM composition administration being the greatest.

The improvement with ECM composition administration alone was also substantial in view of a lower starting point, having no evidence after infarct of improvement.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method of treating a cardiovascular disorder in a subject, comprising:
   providing an extracellular matrix (ECM) composition comprising acellular bioremodelable mesothelial tissue, said mesothelial tissue comprising endogenous proteoglycans, transforming growth factor-β (TGF-β) and vascular endothelial growth factor (VEGF) that collectively induce myofibroblast and stem cell migration, and differentiation of said stem cells into cardiomyocytes when administered to damaged cardiovascular tissue;
   providing a mechanical circulatory support (MSC) device that is configured to support ventricular function of a mammalian heart when connected thereto;
   connecting said MSC device to said subject's circulatory system;
   administering said ECM composition proximate damaged cardiovascular tissue of said subject's heart, wherein said ECM composition induces neovascularization and bioremodeling of said subject's damaged cardiovascular tissue; and
   providing support of ventricular function of said subject's heart with said MSC device.

2. The method of claim 1, wherein said ECM composition is administered directly to said subject's damaged cardiovascular tissue.

* * * * *